(12) United States Patent
Kohayase et al.

(10) Patent No.: US 7,719,672 B2
(45) Date of Patent: May 18, 2010

(54) MACRO INSPECTION APPARATUS AND MICROSCOPIC INSPECTION METHOD

(75) Inventors: Atsushi Kohayase, Kamakura (JP); Mitsuru Uda, Yokohama (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/327,222

(22) Filed: Dec. 3, 2008

(65) Prior Publication Data

US 2009/0147248 A1   Jun. 11, 2009

(30) Foreign Application Priority Data

Dec. 10, 2007   (JP) .............................. 2007-318735

(51) Int. Cl.
*G01N 21/88* (2006.01)
(52) U.S. Cl. ............... 356/237.2; 356/237.1; 356/237.3
(58) Field of Classification Search ... 356/237.1–237.6, 356/394; 250/559.4, 559.41, 559.45, 559.39
See application file for complete search history.

(56) References Cited

U.S. PATENT DOCUMENTS 5,917,588 A * 6/1999 Addiego ................. 356/237.2
6,710,320 B2 * 3/2004 Kurata ..................... 250/208.1
6,753,542 B2 * 6/2004 Ota ........................ 250/559.45
6,963,394 B2 * 11/2005 Yamamoto et al. ........ 356/237.4
7,072,034 B2 * 7/2006 Rosengaus et al. ....... 356/237.5
2004/0173305 A1   9/2004 Sato et al.

FOREIGN PATENT DOCUMENTS

JP   2004-237547 A   8/2004

* cited by examiner

*Primary Examiner*—Sang Nguyen
(74) *Attorney, Agent, or Firm*—Douglas Lashmit; Hoffman Warnick LLC

(57) ABSTRACT

The invention provides a macro inspection apparatus including: a stage on which an inspection object is placed; a light source that irradiates light on an upper surface of the inspection object from an angular direction arbitrarily selected relative to the upper surface of the inspection object; and a line sensor which is placed in an angular direction selected relative to the upper surface of the inspection object so that an optical axis thereof corresponds with an edge of the upper surface area irradiated by the light source and which receives reflected light from the edge of the upper surface area of the inspection object.

10 Claims, 5 Drawing Sheets

MACRO INSPECTION APPARATUS AND MICROSCOPIC INSPECTION METHOD

FIELD OF THE INVENTION

The present invention relates to a macro inspection apparatus and method that inspects the surface flatness of an inspection object, and more particularly to a macro inspection apparatus and method that inspects the flatness of a thin film on a substrate.

BACKGROUND ART

Inspections conducted in the process of fabricating semiconductor, liquid crystals or the like include a macro inspection. In the macro inspection, typically, a human visually spots a defect (flatness, the presence/absence of a scratch, or the like) on the surface of a fabricated film or the like. The macro inspection is an effective inspection because a defect can be spotted over a wide area all at once under the limitations of visual inspection.

As a macro inspection for inspecting the flatness of a film, i.e., a variation (non-uniformity) in film thickness, there has hitherto been conducted an inspection using interference light. In the inspection using interference light, narrow-wavelength light is irradiated to a film and then interference light from the film is detected. However, this method cannot be used for a film in which no interference occurs or a film through which no light is transmitted. That is, the conventional method using interference light has a limitation that only a light transmitting film can be inspected.

A related art surface defect macro inspection apparatus has been described, for example, in Published Unexamined Patent Application No. 2003-28621. This document discloses a surface defect inspection apparatus which arranges a photo-detecting unit at a position which does not receive specular reflection light of inspection illumination light and at the same time efficiently receives scattering light thereof.

SUMMARY OF THE INVENTION

The present invention provides a macro inspection apparatus that inspects the surface flatness of an inspection object with a high sensitivity. The macro inspection apparatus includes: a stage on which the inspection object is placed; a light source for irradiating light on an upper surface of the inspection object from an angular direction arbitrarily selected relative to the upper surface of the inspection object; and a line sensor, placed in an angular direction selected relative to the upper surface of the inspection object so that an optical axis thereof corresponds with an edge of the upper surface area irradiated by the light source, for receiving reflected light from the edge of the upper surface area.

The present invention provides a macro inspection method that inspects the surface flatness of an inspection object by use of a light source and a line sensor, the method including: setting the light source at an angle arbitrarily selected relative to an upper surface of the inspection object and irradiating light on the upper surface; setting the line sensor at an angle selected relative to the upper surface of the inspection object so that an optical axis of the line sensor corresponds with an edge of the upper surface area irradiated by the light source; and causing the line sensor set at the selected angle to receive reflected light from the edge of the upper surface area.

BRIEF DESCRIPTION OF THE DRAWINGS

The novel and inventive features believed characteristic of the invention are set forth in the appended claims. The invention itself, however, as well as modes of use, further objects, and advantages thereof, will best be understood by reference to the following detailed description of an illustrative detailed embodiment when read in conjunction with the accompanying drawings.

FIGS. 2a and 2b, is a view illustrating a positional relationship between the light source and line sensor camera of the macro inspection apparatus of FIG. 1.

DETAILED DESCRIPTION OF THE INVENTION

Figure 1:
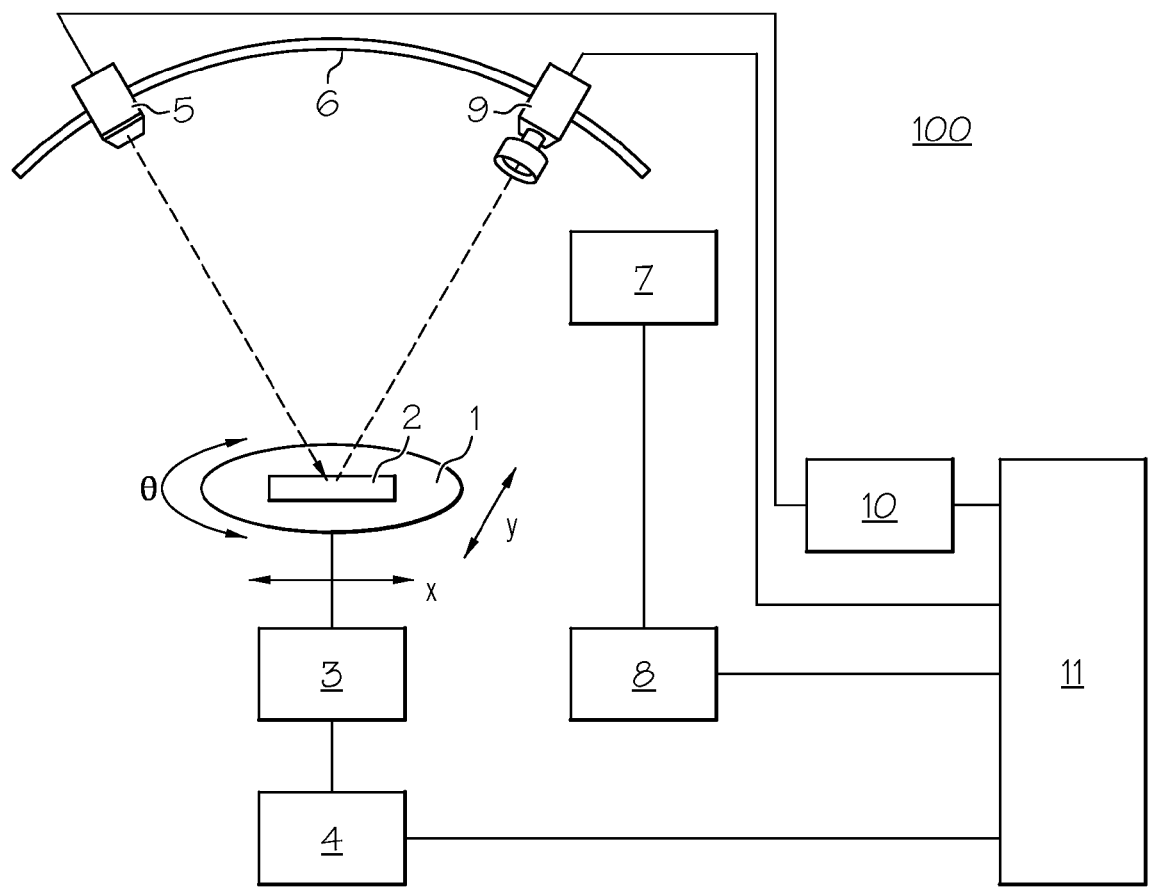
FIG. 1 is a view illustrating a macro inspection apparatus according to an embodiment of the present invention.

FIG. 1 is a view illustrating a macro inspection apparatus 100 according to an embodiment of the present invention. Referring to FIG. 1, an inspection object 2 is placed on a stage 1 of a circular shape. The stage 1 is rotated (θ) or moved in a horizontal (x) direction or a vertical (y) direction by a linear motor 3 under control of a stage controller 4. The light source 5 is moved along a rail 6 of an arc shape by a stepping motor 7 under control of a controller 8. The angle of the light source 5 is arbitrarily set relative to the upper surface of the inspection object 2 placed on the stage 1. The brightness of the light source is varied by a power supply 10 for light source. A line sensor camera 9 is moved, similarly to the light source 5, along the arc shaped rail 6 by the stepping motor 7 under control of the controller 8. The output of the line sensor camera 9 is inputted to an image processing unit 11. The image processing unit 11 controls the stage controller 4, controller 8, line sensor camera 9, and power supply 10 for light source.

Stage 1 has a structure by which reflected light from anywhere other than the surface of the inspection object 2 is hardly produced. More specifically, when the inspection object 2 is transparent and at the same time scattered light is sufficiently produced on the surface thereof, stage 1 is composed of a material acting as a mirror surface with respect to the light (wavelength) of the light source 5. When the surface of the inspection object 2 is a mirror surface and at the same time no scattered light is produced on the surface, stage 1 is composed of a lusterless material which absorbs the light (wavelength) of the light source 5. A thin film on semiconductor substrate (semiconductor wafer), liquid crystal layer on glass substrate, hard disk or patterned media, for example, corresponds to the inspection object 2. However, the inspection object 2 is not limited to these, and any object having a predetermined surface area may be inspected.

The light source 5 can irradiate light so that a vertically long (linear shaped) irradiated area having, for example, a rectangular shape can be formed on the surface of the inspection object 2. In other words, the light source 5 can form an irradiated area containing a linear shaped edge of a predetermined length on the surface of the inspection object 2. The length of the edge is determined according to the size of the inspection object 2, the number of pixels of the line sensor camera 9, and the like. The light source 5 may be constituted of any of an electric bulb type light source such as a halogen bulb, and a light source obtained by arraying light emitting devices such as LED in a line shape. Irrespective of the configuration of the light source 5, the light source 5 also includes an optical system containing a lens and the like.

The line sensor camera 9 includes a sensor obtained by arraying photo-detecting devices (pixels) such as CCD in a line shape. The line sensor camera 9 includes an optical system containing a lens and the like which guides reflected light from the surface of the inspection object 2 to the photo-detecting devices (pixels). The angle of the light source 5 and line sensor camera 9 relative to the surface of the inspection object 2 can be varied every predetermined minimum control angle $\Delta\theta$ by the stepping motor 7. The minimum control angle $\Delta\theta$ obtained by the stepping motor 7 is $\frac{1}{100}$ degrees or less. The minimum control angle is preferably minimized.

The image processing unit 11 processes image information sent from the line sensor camera 9 based on a predetermined measurement program. The image processing unit 11 controls the controllers 4 and 8 and the illumination power supply 10. The image processing unit 11 includes a card (circuit substrate) used to control the line sensor camera 9, a card (circuit substrate) used to control the controllers 4 and 8 and the illumination power supply 10, and a memory used to store image data. A personal computer (PC) including a display corresponds to the image processing unit 11, for example.

Figure 2:
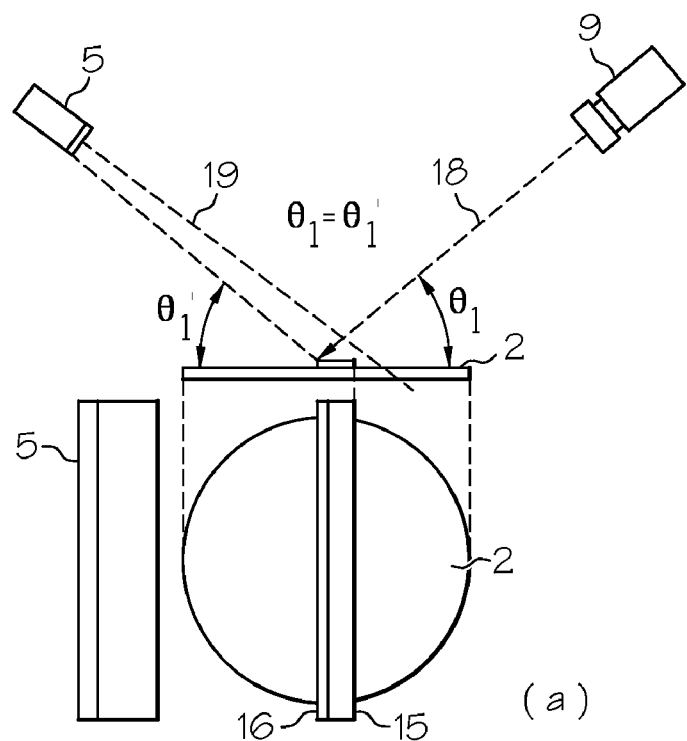
FIG. 2, comprising
Figure 2:
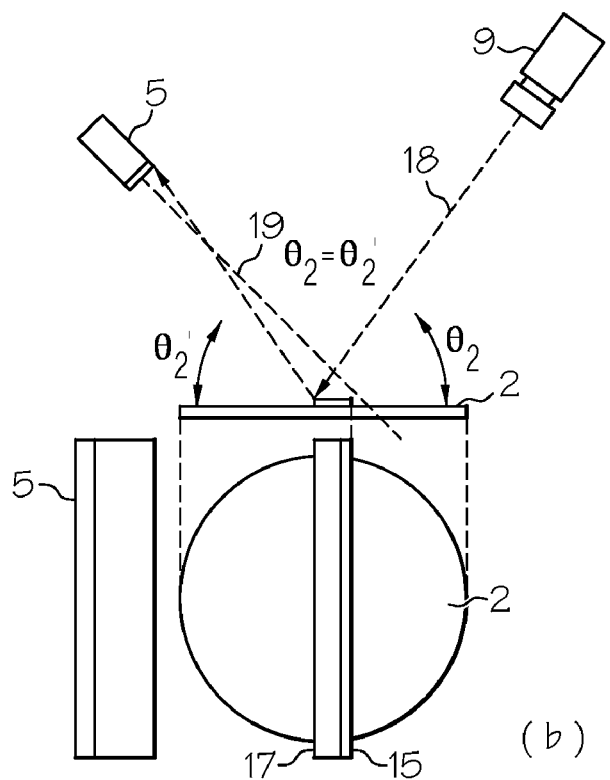

FIG. 2 is a view illustrating an example of positional relationship between the light source 5 and line sensor camera 9 of the macro inspection apparatus 100 illustrated in FIG. 1. On the surface of the inspection object 2, there is projected an illumination area 15 produced by the light source 5, i.e., there is projected the light source itself. FIG. 2(*a*) illustrates a case where an optical axis 18 of the line sensor camera 9 corresponds with a left edge area 16 of the illumination area 15; and FIG. 2(*b*) illustrates a case where an optical axis 18 of the line sensor camera 9 corresponds with a right edge area 17 of the illumination area 15. In FIGS. 2(*a*) and 2(*b*), the upper diagram is a side view, and the lower diagram is a top view. Reference numeral 19 denotes an optical axis of the light source. The optical axis 19 of the light source does not correspond with the optical axis 18 of the line sensor camera 9. That is, the line sensor camera 9 is arranged at a position (angle) at which the optical axis is displaced from specular reflection light from the surface of the inspection object 2.

As illustrated in FIG. 2, the macro inspection apparatus 100 is characterized in that the optical axis 18 of the line sensor camera 9 is made to correspond with the edges 16 and 17 of the area 15 irradiated by the light source 5. One reason for that is that it has been found from an experiment that reflected light from the edge has a significantly great directivity. According to the present invention, the state (flatness) of the surface of the inspection object 2 is detected by using reflected light from the great-directivity edge. It is noted that not only the edge of the illumination area but also a prescribed area (of a small width) containing that edge correspond to the edge according to the present application.

In order to detect reflected light from the great-directivity edge, the following relationship is satisfied. That is, when the size of pixel of the line sensor camera 9 is d, the optical magnification is M, the length of the optical axis 18 is R, and the minimum angle which can be regulated by the stepping motor 7 is $\Delta\theta$, $$d/M \leq 2R \sin(\Delta\theta/2) \quad (1)$$

is satisfied. Here, optical magnification M is a parameter calculated by $$M = L/F \quad (2)$$

where L is the length of line sensor camera (for example, for CCD, pixel size×the number of pixels) and F is effective visual field. Optical magnification M varies depending on a lens mounted in the line sensor camera. For example, in a case of a 85-mm lens, an object distance (the distance from the substrate to the lens) of 1000 mm, a pixel size of 14 μm and the number of pixels being 2048, L=28.672 mm and F=305.272 mm. Thus, M=28.672/305.272=0.0939.

Formula (1) indicates that, in order to detect great-directivity reflected light, conceptually, the line sensor camera 9 is disposed distant by a prescribed distance or more from the inspection object 2. In other words, formula (1) indicates that, when reflected light (light flux) from the surface of the inspection object 2 is considered as one vector for the convenience of explanation, if the pixel size of the line sensor camera 9 is larger than the minimum movement angle $\Delta\theta$ of the camera 9 (i.e., if the length of the optical axis 18 is small), light flux other than the vector increases and thus great-directivity reflected light cannot be captured. In this case, the surface flatness of the inspection object 2 cannot be accurately detected.

In formula (1), for example, when the pixel size is 10 μm and minimum regulatable angle $\Delta\theta$ is 0.01 degrees, the length R of the optical axis 18 is 573 mm or more. Here, the optical magnification of the macro inspection optical system is 0.1.

Figure 3:
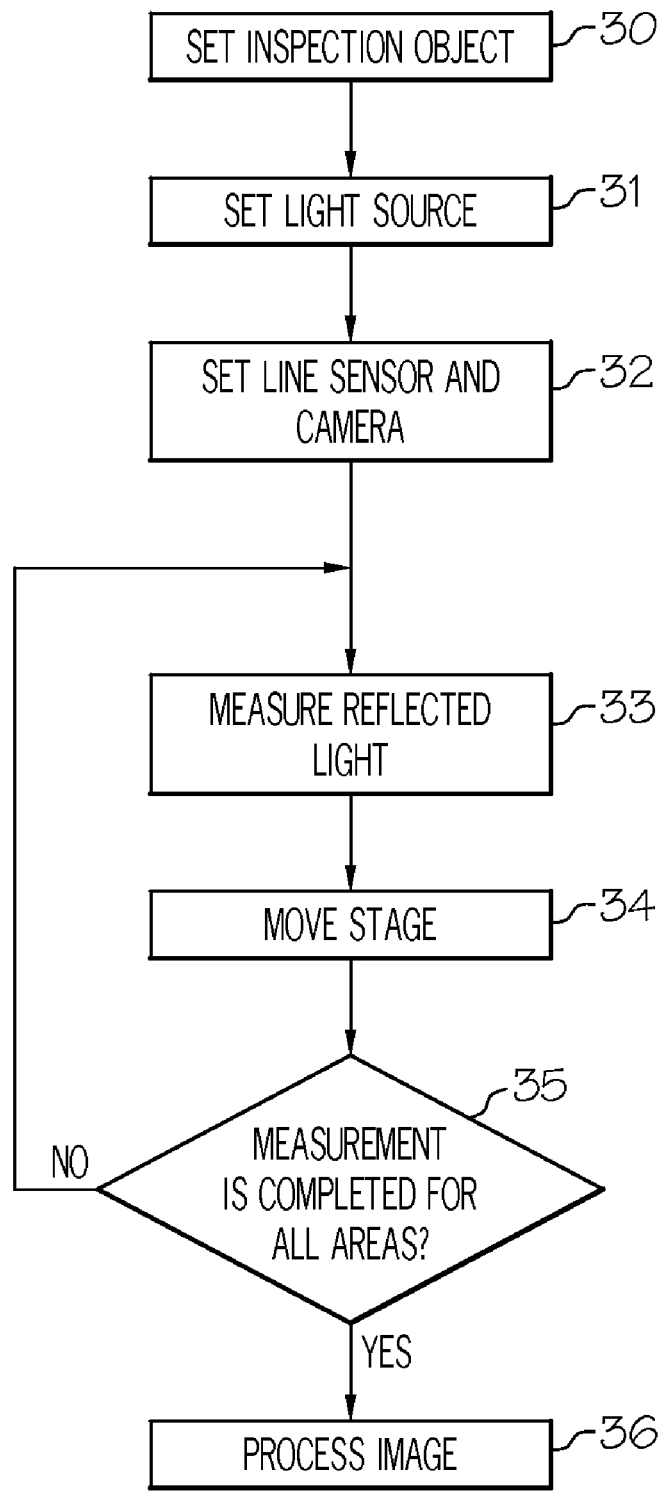
FIG. 3 is a view illustrating the control procedure performed by the image processing apparatus of FIG. 1.

One embodiment of a macro inspection method according to the present invention will now be described by taking as an example, the macro inspection apparatus of FIG. 1. FIG. 3 illustrates the control procedure performed by the image processing unit 11 of FIG. 1. This control procedure is executed by a program stored in the memory of the image processing unit 11. The inspection object 2 is set on the stage 1 (step 30). Then, the stage 1 is moved to cause the inspection object 2 to move to a first measurement position. The light source 5 is set at a predetermined angle (step 31). In this case, the light source 5 is set so that the light flux thereof is thrown on the first measurement position of the inspection object 2. The line sensor camera 9 is set at a predetermined angle (step 32). In this case, the line sensor camera 9 is set so that the optical axis thereof corresponds with the edge (reference numerals 16 and 17 of FIG. 2) of the illumination area produced by the light source 5 on the upper surface of the inspection object 2. The setting of the line sensor camera 9 will be further described in detail later.

The line sensor camera 9 measures reflected light from the surface of the inspection object 2 (step 33). The measurement result (reflected light data) is stored in the memory of the image processing unit 11. In this case, the reflected light data is first sent as brightness data to the image board (circuit substrate) in the image processing unit 11. Thereafter, the brightness data is sent on a per unit basis (for example, brightness data corresponding to one line) from the image board to the memory in the image processing unit 11, and stored in the memory. The stage 1 moves to a subsequent measurement position on the surface of the inspection object 2 (step 34). At this time, the illumination area on the surface of the inspection object 2 moves a predetermined distance. The line sensor camera 9 measures reflected light from surface of the inspection object 2 (step 33). The measurement of reflected light (step 33) and the movement of the stage 1 (step 34) are repeated to perform measurement for all the measurement areas on the surface of the inspection object 2 (step 35).

The brightness data stored in the memory is converted into a bit map format, and thereafter stored in another memory (hard disk or the like) in the image processing unit 11 (step 36). When the image processing is performed, a result (image) of macro surface inspection of the inspection object 2 is obtained. The image processing (step 36) may be performed for each reflected light measurement (step 33) or on a per multiple-measurement basis. In the latter case, multiple results of image processing (of a bit map format) are finally combined (edited) as one piece of image.

Figure 4:
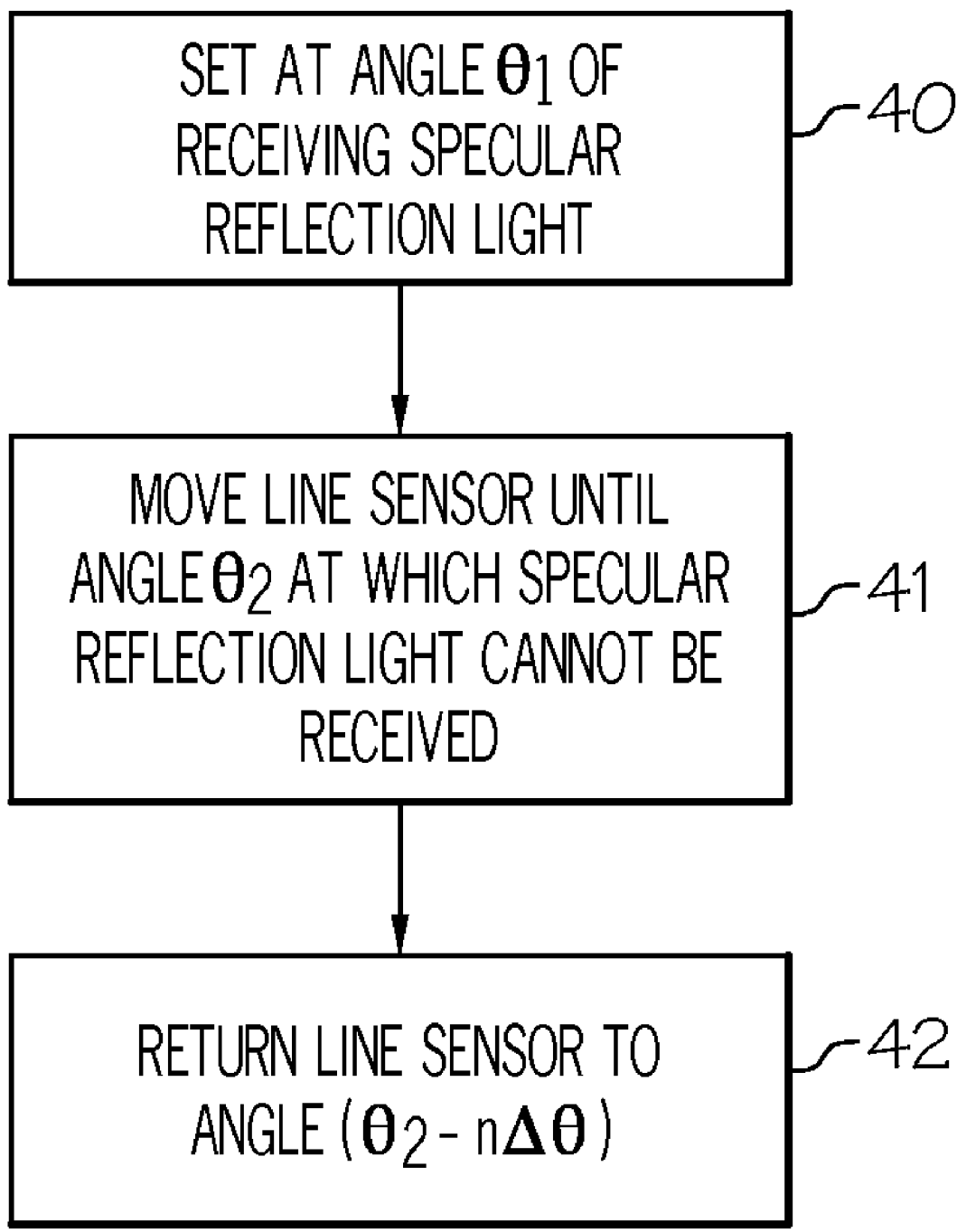
FIG. 4 is a view illustrating the procedure of setting the line sensor camera of FIG. 3.

FIG. 4 is a flowchart illustrating details of the setting (step 32) of the line sensor camera 9. The line sensor camera 9 is set at an angle $\theta_1$ at which reflected light from the edge 16 (17) of the illumination area 15 on the surface of the inspection object 2 can be received (step 40). While the angle of the line sensor camera 9 is varied every minimum control angle $\Delta\theta$, the line sensor camera 9 is moved until angle $\theta_2$ at which specular reflection light cannot be received is reached (step 41). The line sensor camera 9 is returned to an angle $(\theta_2 - n\Delta\theta)$ obtained by subtracting an angle $n\Delta\theta$ (n being any natural number) from the angle $\theta_2$ (step 42). The value of n is arbitrarily set according to the surface state and the like of the inspection object 2 so that higher detection sensibility is obtained.

Figure 5:
FIG. 5 is a view illustrating a result of measurement performed by the macro inspection apparatus of FIG. 1.

FIG. 5 illustrates a result of measuring the surface of a semiconductor wafer by use of the macro inspection apparatus of FIG. 1 in a state (vacuum sticking) where the semiconductor wafer is stuck to a stage (sticking board). Referring to FIG. 5, the especially bright part is convex; the dark part is concave. Distortions, concaves and convexes and the like on the whole surface of the wafer could be macroscopically inspected.

The embodiment of the present invention has been described by taking as an example, FIGS. 1 to 5. However, the present invention is not limited thereto. The present invention can be implemented by embodiments with many improvements, changes or modifications applied thereto conceived by those skilled in the art without departing from the gist of the invention.

The invention claimed is:

1. A macro inspection apparatus for inspecting a surface flatness of an inspection object, the apparatus comprising:
    a stage on which the inspection object is placed;
    a light source for irradiating light on an upper surface of the inspection object from an angular direction arbitrarily selected relative to the upper surface of the inspection object; and
    a line sensor, placed in an angular position selected relative to the upper surface of the inspection object so that an optical axis thereof corresponds with an edge of the upper surface area irradiated by the light source, for receiving reflected light from the edge of the upper surface area, wherein when a pixel size of the line sensor is d, an optical magnification is M, a length of the optical axis is R, and a minimum regulatable angle is $\Delta\theta$, $$d/M \leq 2R \sin(\Delta\theta/2)$$

is satisfied.

2. The macro inspection apparatus according to claim 1, wherein the upper surface area irradiated by the light source contains a linear shaped edge of a predetermined length.

3. The macro inspection apparatus according to claim 1, wherein the light source comprises a linear shaped light source.

4. The macro inspection apparatus according to claim 1, wherein the light source comprises an optical system for forming an illuminated area containing a linear shaped edge of a predetermined length on the upper surface of the inspection object.

5. The macro inspection apparatus according to claim 1, wherein the inspection object includes a thin film formed on a surface of a substrate.

6. The macro inspection apparatus according to claim 1, wherein a surface of the stage comprises a mirror surface or a surface which absorbs incident light.

7. The macro inspection apparatus according to claim 1, further comprising:
    an image processor for receiving an output signal of the line sensor and producing an image corresponding to the amount of reflected light received by the line sensor;
    a light source drive system for varying the angle of the light source;
    a line sensor drive system for varying the angle of the line sensor; and
    a moving system for moving the stage.

8. A macro inspection method for inspecting a surface flatness of an inspection object by use of a light source and a line sensor, the method comprising:
    setting the light source at an angle arbitrarily selected relative to an upper surface of the inspection object and irradiating light on the upper surface;
    setting the line sensor at an angle selected relative to the upper surface of the inspection object so that an optical axis of the line sensor corresponds with an edge of the upper surface area irradiated by the light source; and
    causing the line sensor set at the selected angle to receive reflected light from the edge of the upper surface area, wherein when a pixel size of the line sensor is d, an optical magnification is M, a length of the optical axis is R, and a minimum regulatable angle is $\Delta\theta$, $$d/M \leq 2R \sin(\Delta\theta/2)$$

is satisfied.

9. The macro inspection method according to claim 8, wherein:
    in the setting of the line sensor, the line sensor is set at an angle $\theta_1$ at which specular reflection light from the upper surface of the inspection object can be received;
    while the angle of the line sensor is varied every minimum control angle $\Delta\theta$, the line sensor is moved until an angle $\theta_2$ at which specular reflection light cannot be received is reached; and
    the line sensor is returned to an angle $(\theta_2 - n\Delta\theta)$ obtained by subtracting an angle $n\Delta\theta$ (n being any natural number) from the angle $\theta_2$.

10. The macro inspection method according to claim 8, further comprising:
    moving the inspection object so that the upper surface illumination area produced by the light source moves a predetermined distance, wherein the moving of the inspection object and the receiving of reflected light from the upper surface illumination area of the inspection object are alternately repeated until the measurement of the upper surface of the inspection object is completed.

* * * * *